United States Patent [19]

Barton et al.

[11] Patent Number: 4,518,780

[45] Date of Patent: May 21, 1985

[54] PROCESS FOR THE PREPARATION OF 2-(5,5-DISUBSTITUTED-4-OXO-2-IMIDAZOLIN-2-YL)NICOTINIC ACIDS AND QUINOLINE-3-CARBOXYLIC ACIDS

[75] Inventors: Jerry M. Barton, East Windsor; Don W. Long; Kenneth D. Lotts, both of Trenton, all of N.J.

[73] Assignee: American Cyanamid Company, Stamford, Conn.

[21] Appl. No.: 489,400

[22] Filed: May 5, 1983

Related U.S. Application Data

[63] Continuation-in-part of Ser. No. 381,818, May 25, 1982, abandoned.

[51] Int. Cl.³ ............................................. C07D 401/04
[52] U.S. Cl. .................................... 546/167; 546/278; 546/112; 546/183; 548/302; 548/322
[58] Field of Search ............... 546/167, 278, 112, 183; 548/302, 322

[56] References Cited

U.S. PATENT DOCUMENTS 4,017,510  4/1977  Los ........................................ 548/302

OTHER PUBLICATIONS

Beilstein's Handbuch, vol. 22, pp. 150-151 (1935).
Wagner et al., Synthetic Org. Chem., Wiley, (1953), p. 570.
Hoffman, Imidazole and its Derivatives—Part I, Interscience (1953), pp. 95, 98 and 99.
Noller, Org. Synthesis, Coll. vol. II, p. 586, (1943).
West, J. Am. Chem. Soc., vol. 42, p. 1662 (1920).

*Primary Examiner*—Alan L. Rotman
*Assistant Examiner*—Bernard I. Dentz
*Attorney, Agent, or Firm*—H. G. Jackson

[57] ABSTRACT

A novel process for the preparation of 2-(5,5-disubstituted-4-oxo or thiono)-2-imidazolin-2-yl)nicotinic acids, quinoline-3-carboxylic acids and benzoic acids by the base-catalyzed cyclization of appropriately substituted 2-carbamoyl nicotinic acids, 3-quinolinecarboxylic, or benzoic acids. The products are useful as herbicides.

8 Claims, 1 Drawing Figure

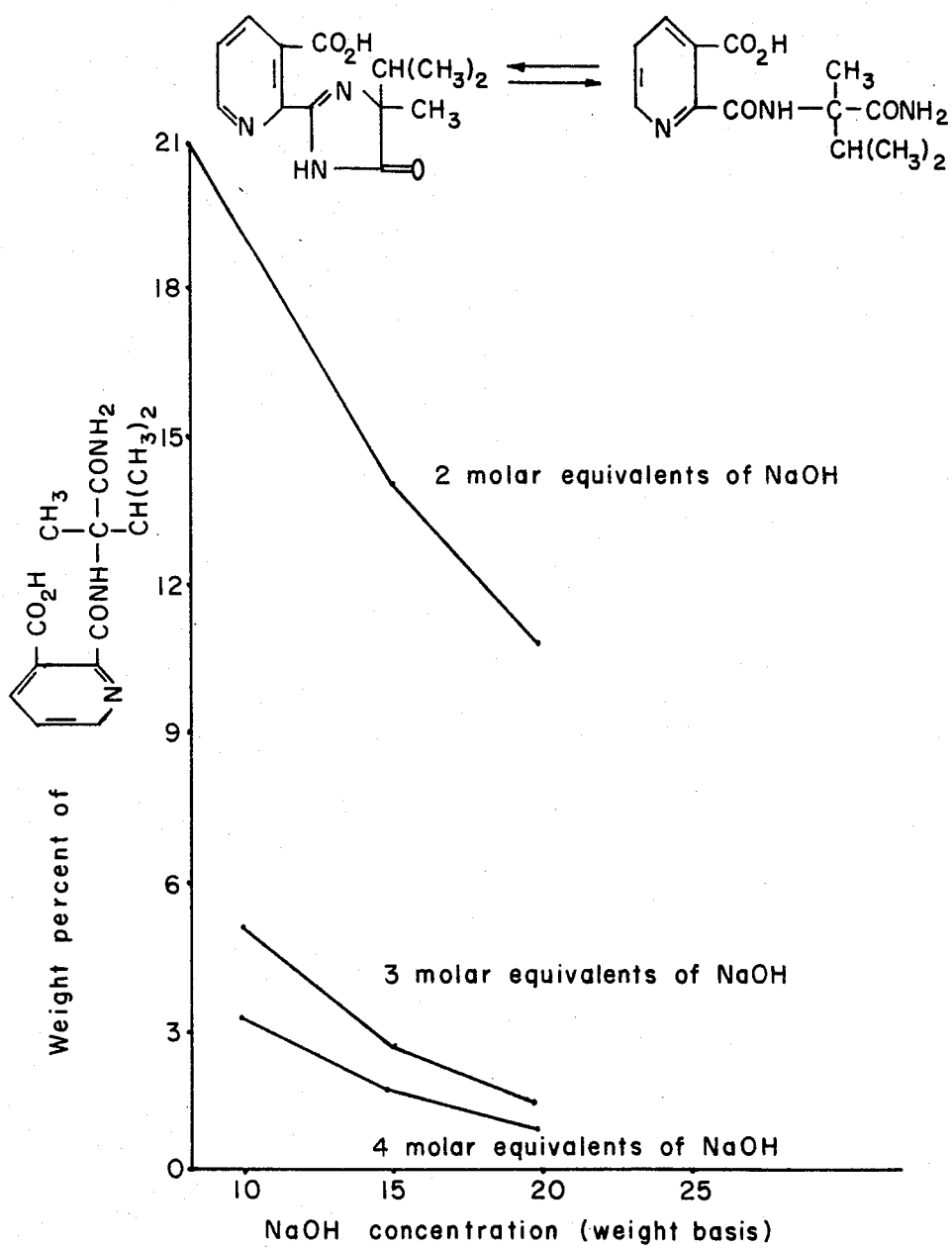
Effect of base concentration and stoichiometry on the formation of 2-(5,5-disubstituted-4-oxo-2-imidazolin-2-yl) compounds.

PROCESS FOR THE PREPARATION OF 2-(5,5-DISUBSTITUTED-4-OXO-2-IMIDAZOLIN-2-YL)NICOTINIC ACIDS AND QUINOLINE-3-CARBOXYLIC ACIDS

This application is a continuation-in-part of pending Ser. No. 381,818, filed May 25, 1982 now abandoned.

SUMMARY OF THE INVENTION

The invention is a method for the preparation of formula (I), 2-(5,5-disubstituted-4-oxo(or thiono)-2-imidazolin-2-yl)nicotinic acids and 3-quinolinecarboxylic acids, having the structure:

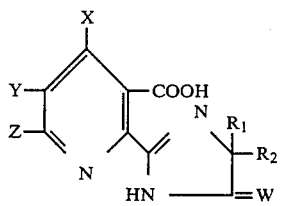
(I)

by the base-catalyzed cyclization of a formula (XVa) 2-carbamoyl nicotinic acid or 2-carbamoyl 3-quinolinecarboxylic acid having the structure:

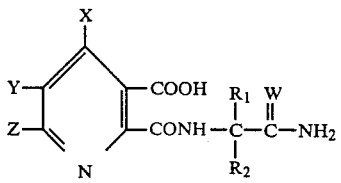
(XVa)

wherein $R_1$ is $C_1-C_4$ alkyl; $R_2$ is $C_1-C_4$ alkyl or $C_3-C_6$ cycloalkyl; and when $R_1$ and $R_2$ are taken together, along with the carbon to which they are attached, they may represent $C_3-C_6$ cycloalkyl optionally substituted with methyl, and when $R_1$ and $R_2$ are not the same, the optical isomers thereof; W is O or S; X is hydrogen, or $C_1-C_4$ alkyl, Y is hydrogen, halogen, $C_1-C_4$ alkyl, $C_1-C_4$ alkoxy, trifluoromethyl, trichloromethyl, difluoromethoxy, diloweralkylamino, $C_1-C_4$ alkylthio, phenyl, phenoxy, or phenyl or phenoxy substituted with one $C_1-C_4$ alkyl, $C_1-C_4$ alkoxy or halogen; Z represents hydrogen, $C_1-C_4$ alkyl, trifluoromethyl, trichloromethyl, phenyl or phenyl substituted with one $C_1-C_4$ alkyl, $C_1-C_4$ alkoxy or halogen; and, when taken together, Y and Z may form a ring in which YZ are represented by the structure: $-(CH_2)_n-$, where n is an integer selected from 3 to 5, provided that X is hydrogen; or YZ is

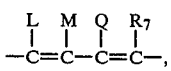

where L, M, Q and $R_7$ each represent hydrogen, halogen, $C_1-C_4$ alkyl, $C_1-C_4$ alkoxy, $C_1-C_4$ haloalkyl, difluoromethoxy, diloweralkylamino, $C_1-C_4$ alkylthio, nitro, phenyl, phenoxy, or mono-substituted phenyl or phenoxy where the substituent is one $C_1-C_4$ alkyl, $C_1-C_4$ alkoxy or halogen; with the proviso that only one of L, M, Q or $R_7$, may represent a substituent other than hydrogen, halogen, $C_1-C_4$ alkyl or $C_1-C_4$ alkoxy.

The base-catalyzed cyclization of this process involves reaction of a formula (XVa) carbamoyl nicotinic acid or carbamoyl 3-quinolinecarboxylic acid having the structure:

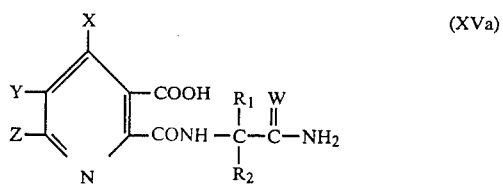
(XVa)

where X, Y, Z, W, $R_1$ and $R_2$ are as described above, with from 2 to 20 moles and preferably 2 to 6 moles of an aqueous or aqueous alcoholic sodium or potassium hydroxide preferably of greater than 10% concentration on a weight basis, per mole of formula (XVa) acid, at a temperature between 25° and 110° C., i.e., reflux temperature. Thereafter, the reaction mixture is acidified to a pH between 2 and 4 to give, in high yield and purity, the 2-(5,5-disubstituted-4-oxo(or thiono)-2-imidazolin-2-yl)nicotinic acid or 3-quinolinecarboxylic acid having the structure of formula (I):

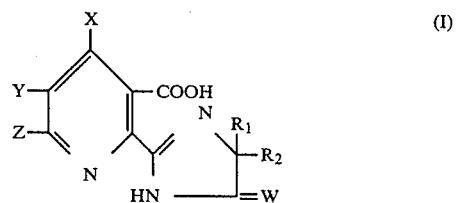
(I)

wherein X, Y, Z, W, $R_1$ and $R_2$ are as described above.

Advantageously, the process of the invention is also effective for preparing the formula (I) 2-(5,5-disubstituted-4-oxo(or thiono)-2-imidazolin-2-yl)-nicotinic acids and 3-quinolinecarboxylic acids from isomer mixtures of the formula (XVa) carbamoyl nicotinic acid or carbamoyl 3-quinolinecarboxylic acid and the formula (XVb) carbamoyl picolinic acid or carbamoyl quinaldic acid. In accordance with the process of the invention, the isomeric mixture containing the formula (XVa) carbamoyl nicotinic acid or quinolinic acid and the formula (XVb) carbamoyl picolinic or quinaldic acid is heated to a temperature between 25° and 110° C. (i.e., reflux temperature) with about 2 to 20 molar equivalents of aqueous or aqueous alcoholic ($C_1-C_4$-alcohol) sodium or potassium hydroxide, and preferably 2 to 6 molar equivalents of said base of greater than 10% concentration on a weight basis under a blanket of inert gas such as nitrogen or argon. The mixture is then cooled to about 25° C. and acidified to a pH between 2 and 4 with a strong mineral acid such as hydrochloric acid or sulfuric acid to give the herbicidally effective formula (I) product in greater than 95% yields. If the formula (XVa) product is insoluble in water, it will be precipitated and can be recovered by filtration. If the product is soluble in water, the mixture can be extracted with an organic solvent such as ether or methylene chloride and the extract concentrated to provide the herbicidally effective 2-(5,5-disubstituted-4-oxo(or thiono)-2-imidazolin-2-yl)nicotinic or 3-quinolinecarboxylic acid encompassed by formula (I). A reaction reported by A. Kjaer, Acta. Chemica. Scand 7, 889, (1953) utilizing dilute 1.0N (4%) aqueous sodium hydroxide gives significantly lower yields (10 to 15% lower).

The process of the invention also relates to a method for the preparation of the herbicidally effective formula (I) 2-(5,5-disubstituted-4-oxo(or thiono)-2-imidazolin-2-yl)nicotinic acids, 3-quinolinecarboxylic acids, and benzoic acids by reaction of an appropriately substituted formula (XVI) anhydride with an aminocarboxamide or aminothiocarboxamide depicted by formula (XIIIa) to yield an isomeric mixture of the formula (XVa) and formula (XVb) carbamoyl nicotinic, quinolinecarboxylic, or benzoic acid and the carbamoyl picolinic or quinaldic acid. This reaction is carried out, preferably using equivalent amounts of the formula (XVI) anhydride and the formula (XIIIa) carboxamide or thiocarboxamide, in the presence of an inert organic solvent such as low-boiling ether (diethyl ether, tetrahydrofuran or dimethoxyethane), acetonitrile, ethyl acetate or a halogenated hydrocarbon such as methylene chloride. The reaction is generally conducted at a temperature between 20° and 80° C. and preferably at 30° to 60° C. under a blanket of inert gas such as nitrogen or argon. This reaction yields the isomeric mixture of the formula (XVa) carbamoyl nicotinic, 3-quinolinecarboxylic, or benzoic acids and the formula (XVb) carbamoyl picolinic or quinaldic acids. The isomeric mixture may then be treated as described above to recover the herbicidally effective formula (IA) 2-(5,5-disubstituted-4-oxo(or thiono)-2-imidazolin-2-yl)-nicotinic acids, 3-quinolinecarboxylic, or benzoic acids.

The above described reactions are graphically illustrated in Flow Diagram I. The process of this invention is described in the copending application for U.S. Letters Patent of Marinus Los, Ser. No. 382,041, filed May 25, 1982 and incorporated herein by reference thereto. This process is also described in the copending application for U.S. Letters Patent of Peter John Wepplo, Ser. No. 381,828, filed May 25, 1982 and incorporated herein by reference thereto.

FLOW DIAGRAM I

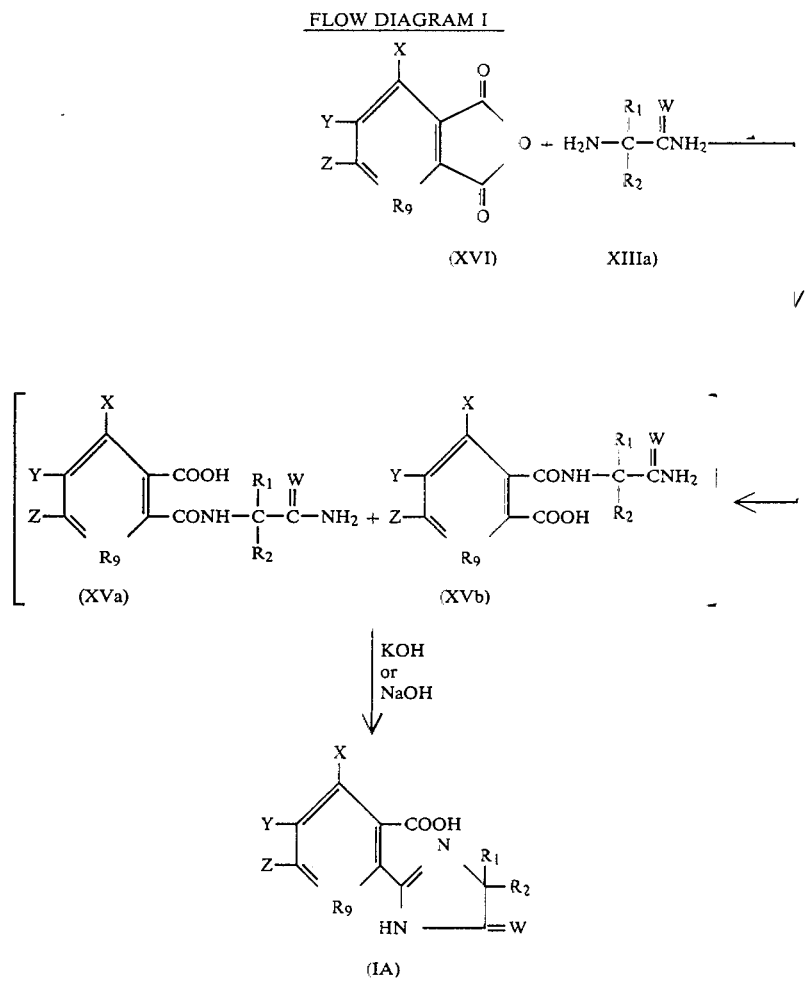

wherein X, Y, Z, W, $R_1$ and $R_2$ are as described above and $R_9$ is N or CH.

Conveniently, the method of the present invention is also suitable for the preparation of the imidazolinylquinolinic, nicotinic, and benzoic acid herbicides directly from nitriles by hydrolysis of the nitrile in situ with a strong base and hydrogen peroxide in a single operation as graphically illustrated below:

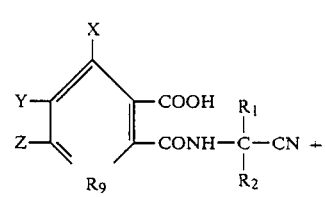

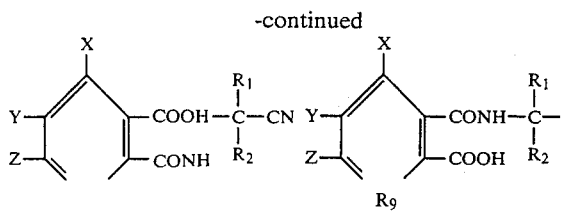

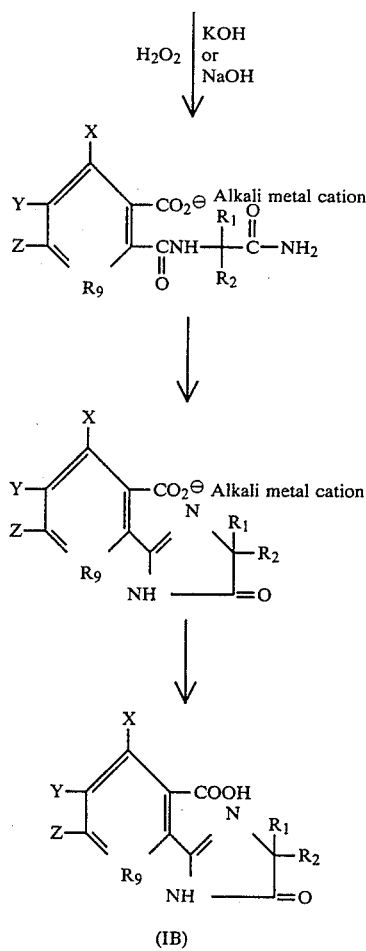

(IB)

wherein $R_9$, X, Y, Z, $R_1$ and $R_2$ are as described above.

The reactions may be carried out at 0°–100° C. in water, a mixture of water and water miscible solvents such as $C_1$–$C_4$ alcohol or a mixture of water and water immiscible solvents such as dichloromethane, 1,2-dichloroethane, chlorobenzene, toluene, xylenes and ethyl ether. The reactions may also be carried out in $C_1$–$C_4$ alcohols without the addition of water. Reactions in water at 60°–100° C. are preferred as cyclization to the desired imidazolinyl products is more rapid at elevated temperatures, and disposal or recovery of organic solvents is not necessary.

The use of aqueous 30–90% hydrogen peroxide with alkali metal hydroxides serves to speed the conversion of the acid amidonitriles to the alkali metal cation salts of the acid diamides and results in less by-product formation. The peroxide may be employed in a molar ratio of 0 to 10 moles, preferably 2 to 5 moles, per mole of acid amidonitrile.

Both aqueous and aqueous alcoholic alkali metal hydroxides such as KOH, NaOH, or $CA(OH)_2$ may be employed in molar ratios of 1 to 10 moles, preferably 2 to 6 moles of 10% or greater concentration on a weight basis, per mole of acid amidonitrile.

The product imidazolinyl-acids are amphoteric and are capable of acting either as acids or bases. Thus, they may be isolated as the alkali metal cation salts, as the free acids, and when treated with strong acids such as hydrochloric, sulfuric and hydrobromic acids, as acid addition salts.

The acid amidonitriles suitable for use as starting materials are conveniently prepared by first reacting methyl isopropyl ketone with hydrogen cyanide in aqueous ammonium hydroxide to obtain 2-amino-2,3-dimethylbutyronitrile as described in the application for U.S. Letters Patent of Walter Stepek and Matthew Nigro, Ser. No. 381,812, filed May 25, 1982, now abandoned and incorporated herein by reference thereto. This compound is then reacted with the appropriate anhydride to give the acid amidonitriles. This preparation is described in U.S. Pat. No. 4,017,510.

The formula (IA) 2-(5,5-disubstituted-4-oxo-(or thiono)-2-imidazolin-2-yl)nicotinic acids, 3-quinolinecarboxylic acids, and benzoic acids, prepared by the process of the present invention, are highly effective herbicidal agents useful for the control of a wide variety of monocotyledonous and dicotyledonous plants.

They are also useful as aquatic herbicides and are unique in their effectiveness in controlling plants when applied to the foliage thereof, or to the soil, or water containing seeds, or other propagating organs of the plants such as tubers, rhizomes or stolons, at rates of from about 0.025 to 8.0 kg/ha, and preferably at rates from about 0.032 to 4.0 kg/ha.

The formula (IA) herbicides can be formulated as wettable powders, flowable concentrates, emulsifiable concentrates, granular formulations, and the like.

Wettable powders can be prepared by grinding together about 20% to 45% by weight of a finely divided carrier such as kaolin, bentonite, diatomaceous earth, attapulgite, or the like, 45% to 80% by weight of the active compound, 2% to 5% by weight of a dispersing agent such as sodium lignosulfonate, and 2% to 5% by weight of a nonionic surfactant, such as octylphenoxy polyethoxy ethanol, nonylphenoxy polyethoxy ethanol, or the like.

A typical flowable liquid can be prepared by admixing about 40% by weight of the active ingredient with about 2% by weight of a gelling agent such as bentonite, 3% by weight of a dispersing agent such as sodium lignosulfonate, 1% by weight of polyethylene glycol and 54% by weight of water.

A typical emulsifiable concentrate can be prepared by dissolving about 5% to 25% by weight of the active ingredient in about 65% to 90% by weight of N-methylpyrrolidone, isophorone, butyl cellosolve, methylacetate, or the like and dispersing therein about 5% to 10% by weight of a nonionic surfactant such as an alkylphenoxy polyethoxy alcohol. This concentrate is dispersed in water for application as a liquid spray.

When the compounds are to be used as herbicides where soil treatments are involved, the compounds may be prepared and applied as granular products. Preparation of the granular product can be achieved by dissolving the active compound in a solvent such as methylene chloride, N-methylpyrrolidone, or the like and spraying the thus-prepared solution on a granular carrier such as corncob grits, sand, attapulgite, kaolin, or the like.

The granular product thus prepared generally comprises about 3% to 20% by weight of the active ingredient and about 97% to 80% by weight of the granular carrier.

In order to facilitate a further understanding of the invention, the following examples are presented primarily for the purpose of illustrating certain more specific details thereof. The invention is not to be deemed limited thereby except as defined in the claims. Unless otherwise noted, all parts are by weight.

EXAMPLE 1

Preparation of 2-(5-isopropyl-5-methyl-4-oxo-2-imidazolin-2-yl)nicotinic acid

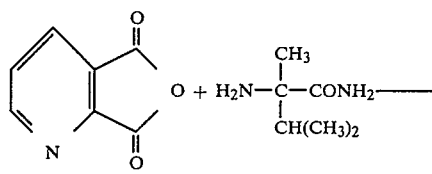

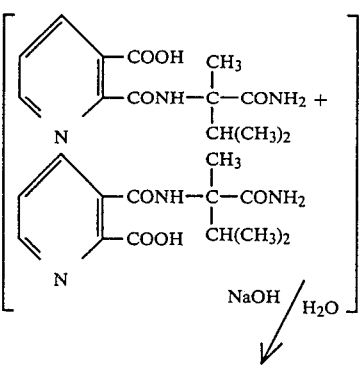

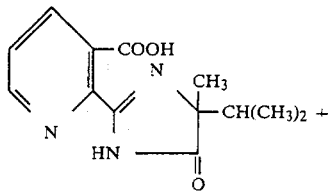

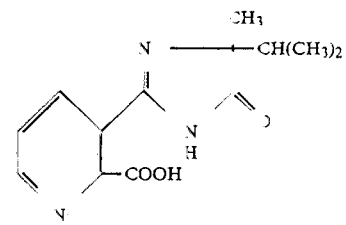

To a stirred suspension of 2,3-pyridinecarboxylic anhydride (30 g) in 150 mL of acetonitrile is added a solution of 2-amino-2,3-dimethylbutyramide (28 g) in 140 mL of acetonitrile at 25° to 30° C. The mixture is stirred for 2 hours. The solvent is removed at 50° C. and reduced pressure. The residual gum is dissolved in 230 mL of 2.6N sodium hydroxide and heated to 80° C. for 1.5 hours.

The mixture is cooled to 25° C. and acidified to a pH of 3 with 65 mL of 37% hydrochloric acid. The resulting solution is extracted with two 200 mL portions of methylene chloride. The extracts are concentrated to a residue of 33 g of the desired product, mp 160°–165° C.

After standing overnight, the aqueous layer deposits 3.8 g of the picolinic acid isomer, mp 155°–157° C. (dec.).

EXAMPLE 2

Preparation of 2-(4-oxo-1,3-diazaspiro[4.5]dec-2-en-2-yl)nicotinic acid

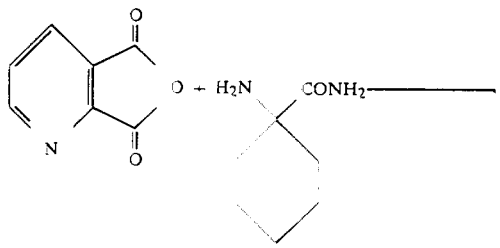

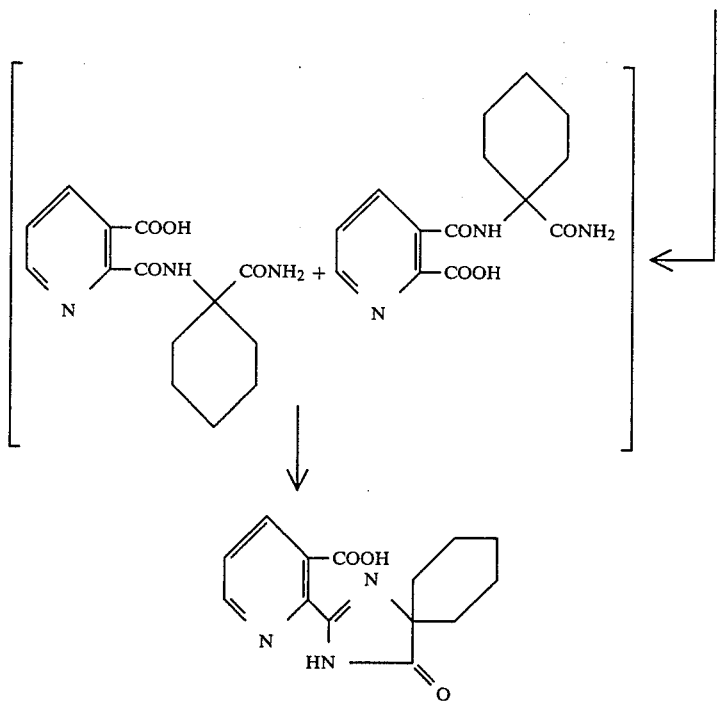

To a stirred solution of 7.1 g of 1-aminocyclohexanecarboxamide in 60 mL of methylene chloride is added 7.5 g of 2,3-pyridinedicarboxylic anhydride. The mixture becomes warm and forms a solution. Stirring is continued for two hours as a colorless solid precipitates. The mixture of monoacids is collected, 12.0 g, mp 168°–178° C. (dec).

This material is dissolved in 45 mL of 2.7N sodium hydroxide and heated for one hour at 80°–85° C. It is then cooled, acidified with 10.3 mL of 37% hydrochloric acid, and extracted with two 25 mL portions of methylene chloride. The extracts are concentrated to give 7.5 g of the desired product which is recrystallized from aqueous methanol to give 2-(4-oxo-1,3-diazaspiro[4.5]dec-2-en-2-yl)nicotinic acid, mp 186°–189° C.

EXAMPLE 3

Preparation of 6-isopropyl-2-(5-isopropyl-5-methyl-4-oxo-2-imidazolin-2-yl)nicotinic acid

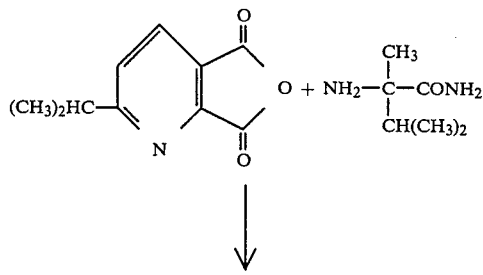

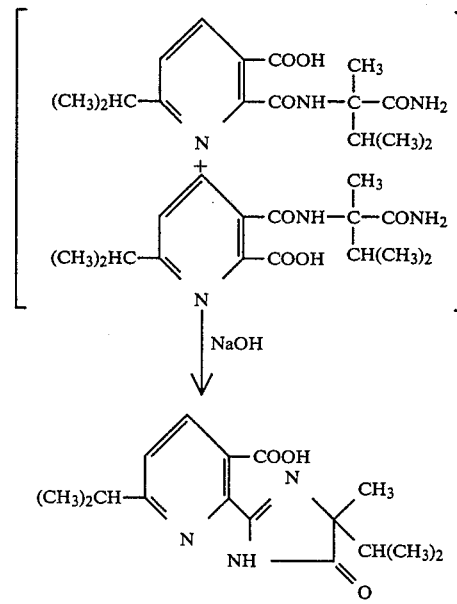

To a stirred solution of the anhydride (15.1 g) in 125 mL THF under nitrogen is added 11.4 g of 2-amino-2,3-dimethylbutyramide. The mixture is stirred overnight. The solvent is removed in vacuo, and the resulting oil (consisting of a mixture of the isomeric pyridine monoacid products) dissolved in 66 mL of 6N NaOH. This solution is heated at 70° C. under nitrogen for three and one-half hours, then cooled and the pH of the solution adjusted to 9 with 6N $H_2SO_4$. The mixture is extracted with ether twice, and the organic extracts discarded. The pH of the aqueous phase is adjusted to 3 with 6N $H_2SO_4$. The resulting precipitate is removed by filtration, washed with water and dried to give 13.25 g of desired product. A sample is recrystallized from methylene chloride-hexane followed by ether-hexane to give an analytically pure sample of 6-isopropyl-2-(5-isopropyl-5-methyl-4-oxo-2-imidazolin-2-yl)nicotinic acid, mp 131°–133.5° C.

By using essentially the same procedure, but substituting the appropriate susbstituted pyridine-2,3-dicarboxylic acid anhydride and also substituting if necessary, the optically active 2-amino-2,3-dimethylbutyramide or the 2-amino-2,3-dimethylthiobutyramide for 2-amino-2,3-dimethylbutyramide, the following nicotinic acids were prepared.

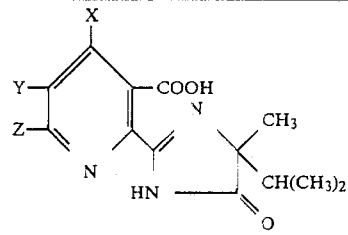

| X | Y | Z | mp °C. |
|---|---|---|---|
| H | H | CH₃ | 145–146.5 |
| H | H | CF₃ | 133–142 |
| H | H | H | 128–131 $[\alpha]_D^{25} = +18.37°$ (c = 0.0902 g/ml THF) |
| H | H | n-C₃H₇ | 148.5–150.5 |
| H | H | Cl-C₆H₄- | 247–249 |
| H | H | CH₃-C₆H₄- | 215.5–218.5 |

-continued

| X | Y | Z | mp °C. |
|---|---|---|---|
| H | H | C₆H₅- | 252–254 |
| H | H | C₂H₅ | 118–122 |
| H | CH₃ | CH₃ | 172–180 |
| H | (CH₂)₃ |  | 160–164 |
| H | H | (CH₂)₄ | 170–172.5 |
| H | H | (CH₂)₄ | 162–165 |
| H | (CH₂)₅ |  | 141–148 | mp 182–184°

EXAMPLE 4

Preparation of 2-(5-isopropyl-5-methyl-4-oxo-2-imidazolin-2-yl)-3-quinolinecarboxylic acid

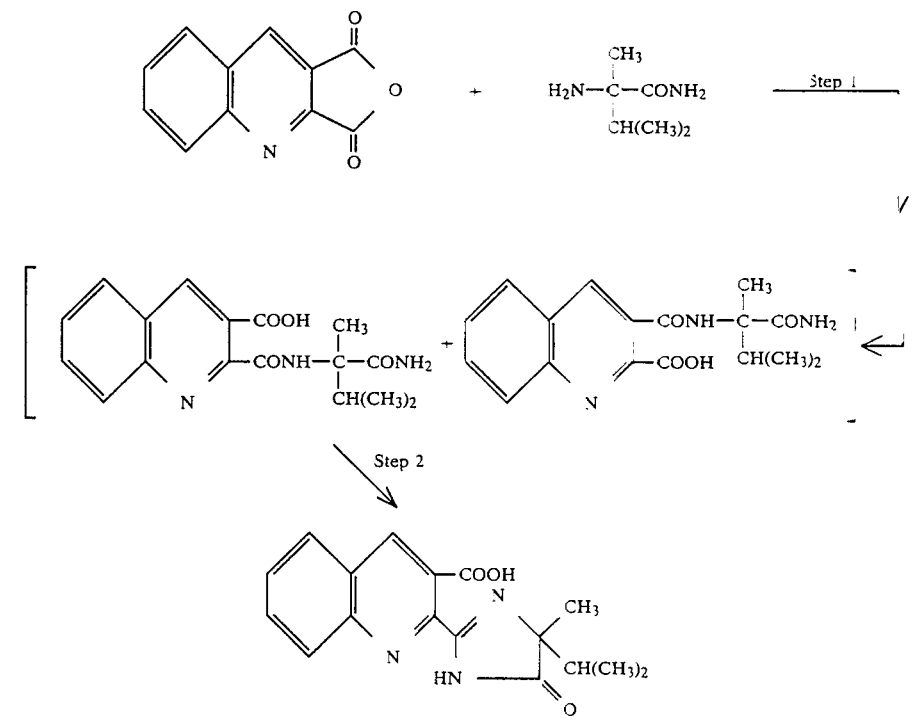

To a stirred solution of 2-amino-2,3-dimethylbutyramide (40 g) in 500 mL of acetonitrile is added 60 g of 2,3-quinolinedicarboxylic acid anhydride in portions during about 45 minutes. The mixture is heated to 50°–60° C. for two hours, cooled to room temperature and filtered to give 73.7 g of the mixture of carbamoyl quinolinecarboxylic acids.

This solid is dissolved in 435 mL of 1.5N sodium hydroxide and heated for two hours at 80°–85° C. The solution is cooled and acidified with 57 mL of 37% hydrochloric acid. The desired product is removed by filtration and dried. The solid is recrystallized from methanol to give 49 g of 2-(5-isopropyl-5-methyl-4-oxo-2-imidazolin-2-yl)-3-quinolinecarboxylic acid mp 240°–242° C.

Following step 1 of the above procedure yields the following 2-carbamoyl-3-quinolinecarboxylic acids having the structure:

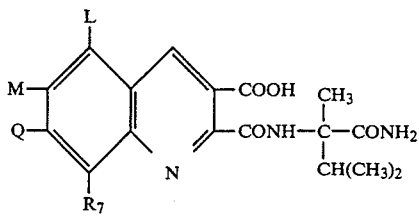

wherein L, M, Q and $R_7$ are as reported below.

| L | M | Q | $R_7$ | mp °C. |
|---|---|---|---|---|
| H | H | H | H | 172.5–173.5 |
| H | H | H | H | 183–185 [$\alpha_D$] = −90.5° in $CH_2Cl_2$ |
| H | $OC_2H_5$ | H | H | — |
| H | $NO_2$ | H | H | 225–227 |
| H | H | H | $OCH_3$ | Foam |
| H | $CF_3$ | H | H | 222–224 |
| H | CN | H | H | — |
| H | $C_6H_5$ | H | H | 189.5–192 |
| H | H | $CH_3$ | $CH_3$ | 246–250 |
| H | $OCH_3$ | H | H | — |
| H | $CH_3$ | $CH_3$ | H | — |
| H | $C_2H_5$ | H | H | 198–199 |
| H | $C_4H_9$ | H | H | 163–164 |
| H | Br | H | H | — |
| $OCH_3$ | H | H | $OCH_3$ | 209–209.5 |
| H | $SCH_3$ | H | H | — |
| H | $OC_6H_5$ | H | H | 189–190 |
| H | $OCF_2H$ | H | H | 194–196 |
| H | H | $OC_2H_5$ | H | — |

Following step 2 of the above procedure, i.e., the base-catalyzed cyclization of a carbamoyl-3-quinolinecarboxylic acid yields the 2-(5-isopropyl-5-methyl-4-oxo-2-imidazolin-2-yl)-3-quinolinecarboxylic acids having the structure:

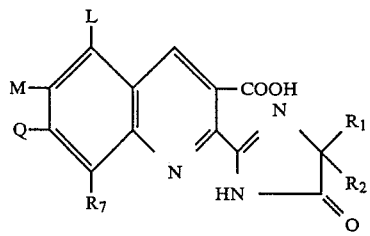

wherein L, M, Q and $R_7$ are as reported below.

| L | M | Q | $R_7$ | mp °C. |
|---|---|---|---|---|
| H | H | H | H | 241–244 |
| H | H | H | H | 228–236.5 [$\alpha$]$_D^{25}$ = +28.3° (c = 0.0105 g/mL $CH_2Cl_2$) |
| H | $OC_2H_5$ | H | H | 206–208 |
| H | $NO_2$ | H | H | 241.5–242 |
| H | H | H | $OCH_3$ | 258–261 |
| H | $CF_3$ | H | H | 215–218 |
| H | CN | H | H | — |
| H | $C_6H_5$ | H | H | 209.5–212 |
| H | H | $CH_3$ | $CH_3$ | 280 |
| H | $OCH_3$ | H | H | 203.5–205 |
| H | $CH_3$ | $CH_3$ | H | 238–240 |
| H | $C_2H_5$ | H | H | 179–180.5 |
| H | $C_4H_9$ | H | H | 149–150.5 |
| H | Br | H | H | 215–225 |
| $OCH_3$ | H | H | $OCH_3$ | 249–250 |
| H | $SCH_3$ | H | H | 264–265 |
| H | H | $OC_2H_5$ | H | — |
| H | $OC_6H_5$ | H | H | 223 |
| H | $OCF_2H$ | H | H | 208–209 |

EXAMPLE 5

Preparation of 2-(5-Isopropyl-5-methyl-4-oxo-2-imidazolin-2-yl)benzoic acid

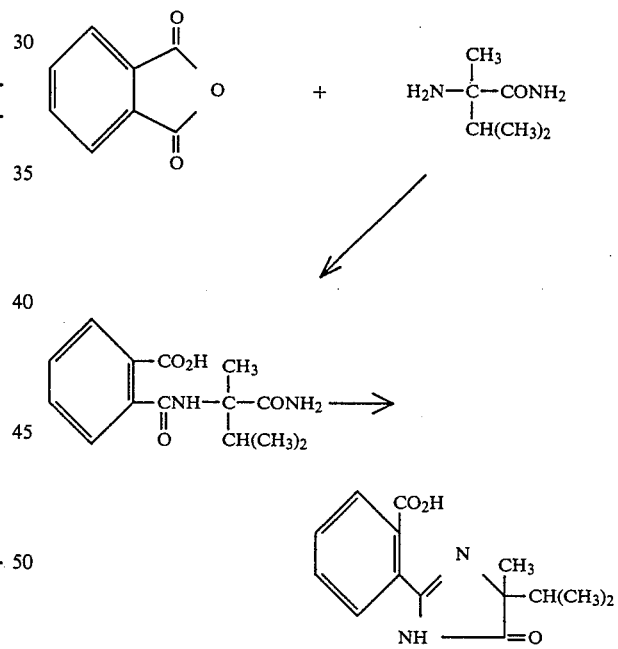

To a stirred solution of 13.4 g of 2-amino-2,3-dimethylbutyramide in 200 mL of methylene chloride is added 13.4 g of phthalic anhydride. The mixture is warmed to reflux for a few minutes and then left to cool and stir overnight. The clear solution is then stirred with 160 mL of 0.8N sodium hydroxide for 15 minutes. The aqueous layer is separated and treated with another 12.1 g of 50% aqueous sodium hydroxide and the alkaline solution is heated to 75° C. for 2.5 hours.

The solution is then cooled to 25° C. and neutralized with 23 mL of 37% aqueous hydrochloric acid. Colorless product separates and is collected and dried to give 13.8 g, mp 158°–162° C. The filtrate is concentrated to a volume of 50 mL at reduced pressure to give another

EXAMPLE 6

Preparation of
2-(5-isopropyl-5-methyl-4-oxo-2-imidazolin-2-yl)-p-toluic acid and
6-(5-isopropyl-5-methyl-4-oxo-imidazolin-2-yl)-m-toluic acid

EXAMPLE 7

Preparation of
2-(5-isopropyl-5-methyl-4-oxo-2-imidazolinyl-2-yl)-p-toluic acid and
6-(5-isopropyl-5-methyl-4-oxo-2-imidazolin-2-yl)-m-toluic acid

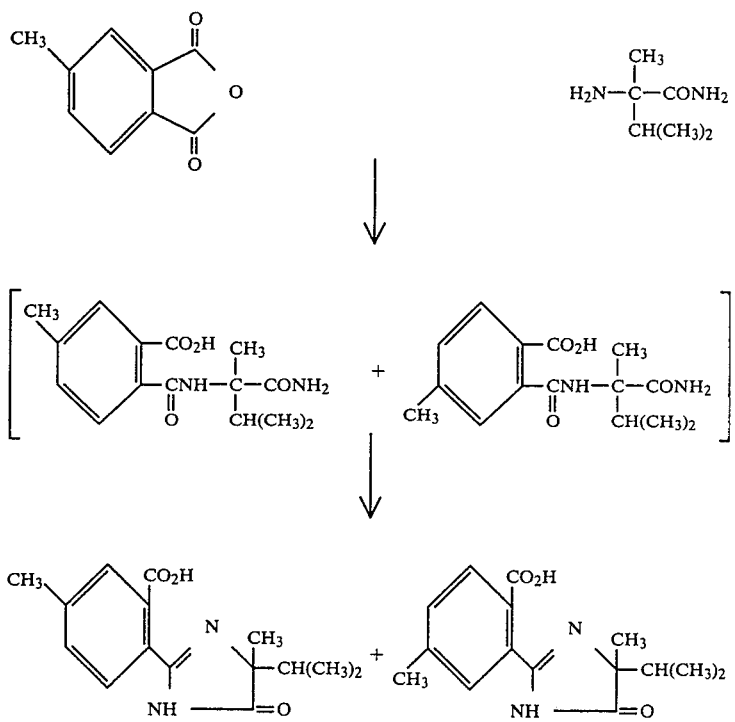

To a solution of 14.4 g of 2-amino-2,3-dimethyl-butyramide in 75 mL of acetonitrile is added 16.2 g of 4-methylphathalic anhydride. The solution is warmed to 60° C. for two hours and then concentrated at reduced pressure to a residue of 31.3 g. The residue is dissolved in 80 mL of 3N sodium hydroxide and warmed to 80°-85° C. for three hours. It is then cooled to 25° C. and neutralized with 23.5 mL of 37% aqueous hydrochloric acid. Near the end of the neutralization, 100 mL of methylene chloride is added to dissolve the gummy product which is separating. The layers are separated and the aqueous layer is extracted with an additional 65 mL of methylene chloride. The combined methylene chloride layers are concentrated to a residual gum weighing 28.8 g which is shown by quantitative high performance liquid chromatography assay to contain 23.9 g of the two desired products. The yield is therefore 87%.

To 32.0 g (0.116 mol) of N-(1-cyano-1,2-dimethyl-propyl)-4(and 5)-methyl phthalamic acid in 30 mL water is added 30.0 g (0.375 mol) of 50% sodium hydroxide. External cooling is applied to hold the temperature at 20°–25° C.; 56.0 g (0.494 moles) of 30% aqueous hydrogen peroxide is added in 30 minutes while maintaining the temperature at 20°–30° C. The solution is heated to 80° C. and stirred at 80°–90° C. until the reaction is complete as determined by thin layer chromatography (approximately two hours). After the reaction mixture is cooled to 20°–30° C., 125 mL of methylene chloride is added and then 19.2 g (0.188 mol) of 96% sulfuric acid is added to neutralize the mixture. The organic layer is separated and the solvent is distilled off to give 31.7 g of 76.7% pure (76.0% yield) of solid 2-(5-isopropyl-5-methyl-4-oxo-2-imidazolin-2-yl)-p-toluic acid and 6-(5-isopropyl-5-methyl-4-oxo-2-imidazolin-2-yl)-m-toluic acid.

EXAMPLE 8

Preparation of 2-(5-isopropyl-5-methyl-4-oxo-2-imidazolinyl-2-yl)-p-toluic acid and 6-(5-isopropyl-5-methyl-4-oxo-2-imidazolin-2-yl)-m-toluic acid

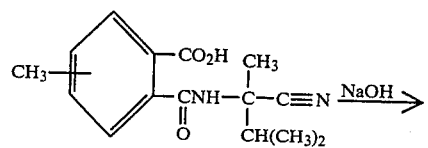

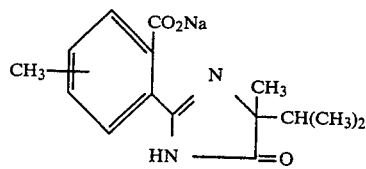

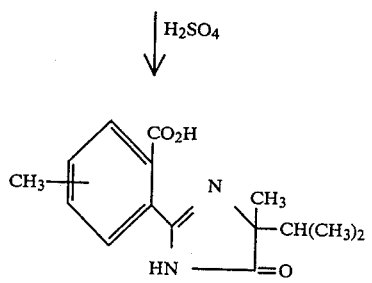

To 29.5 g (0.108 mol) of N-(1-cyano-1,2-dimethylpropyl)-4(and 5)-methyl phthalamic acid in 111 mL of water is added 26.4 g (0.33 mol) of aqueous 50% sodium hydroxide. External cooling is applied to hold the temperature at 20°–25° C. The mixture is stirred for one hour at 20°–25° C. then heated to 80°–90° C. and stirred until the reaction is complete as determined by thin layer chromatography analysis of reaction mixture (approximately seven hours). The reaction mixture is cooled to 20°–30° C. and 125 mL of methylene chloride and 16.8 g (0.165 mol) of 96% sulfuric acid are added to neutralize the mixture. The organic layer is separated and the solvent removed in vacuo to give 26.3 g of 69.3% pure, (61.5% yield) solid 2-(5-isopropyl-5-methyl-4-oxo-2-imidazolin-2-yl)-p-toluic acid and 6-(5-isopropyl-5-methyl-4-oxo-2-imidazolin-2-yl)-m-toluic acid.

EXAMPLE 9

Preparation of 2-(5-isopropyl-5-methyl-4-oxo-2-imidazolin-2-yl)benzoic acid, hydrochloride salt

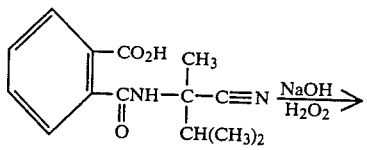

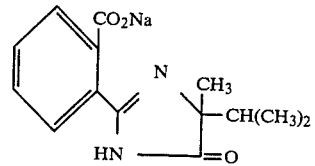

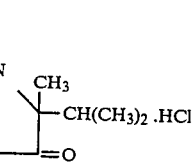

To 5.22 g (0.020 mol) of N-(1-cyano-1,2-dimethylpropyl)phthalamic acid in a mixture of 35 mL isopropyl alcohol and 10 mL of water is added 6.41 g (0.080 mol) of aqueous 50% sodium hydroxide. External cooling is applied to hold the temperature at 20°–30° C. and 4.80 g (0.042 mol) of aqueous 30% hydrogen peroxide is added. The mixture is heated at 80° C. for five hours then cooled to 20°–25° C. Aqueous 36% hydrochloric acid is added to adjust the pH to 1. The volatile solvent is removed in vacuo to give 8.35 g of solid 2-(5-isopropyl-5-methyl-4-oxo-2-imidazolin-2-yl)benzoic acid, hydrochloride salt. The solid is analyzed by high performance liquid chromatography. The real yield is 60.3%.

EXAMPLE 10

Preparation of 2-(5-isopropyl-5-methyl-4-oxo-2-imidazolin-2-yl)nicotinic acid

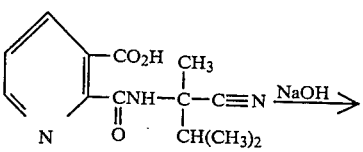

-continued

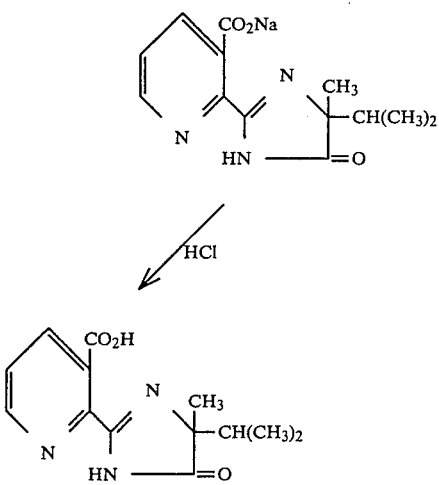

To a stirred mixture of 20 mL of water and 8.40 g (0.105 mol) of 50% sodium hydroxide solution is added 7.83 g (0.030 mol) of 2-[(1-cyano-1,2-dimethylpropyl)aminocarbonyl]nicotinic acid. External heating is applied to raise the temperature to 70°–75° C. where it is maintained for five hours. After cooling the reaction mixture to 20°–30° C., 50 mL of methylene chloride is added and the pH is adjusted to 3.0 by the addition of 37% hydrochloric acid. The organic layer is separated and the solvent is removed by distillation to give 6.71 g of solid 2-(5-isopropyl-5-methyl-4-oxo-2-imidazolin-2-yl)nicotinic acid which is 90% pure in 77% yields.

EXAMPLE 11

Preparation of 2-(5-isopropyl-5-methyl-4-oxo-2-imidazolin-2-yl)nicotinic acid

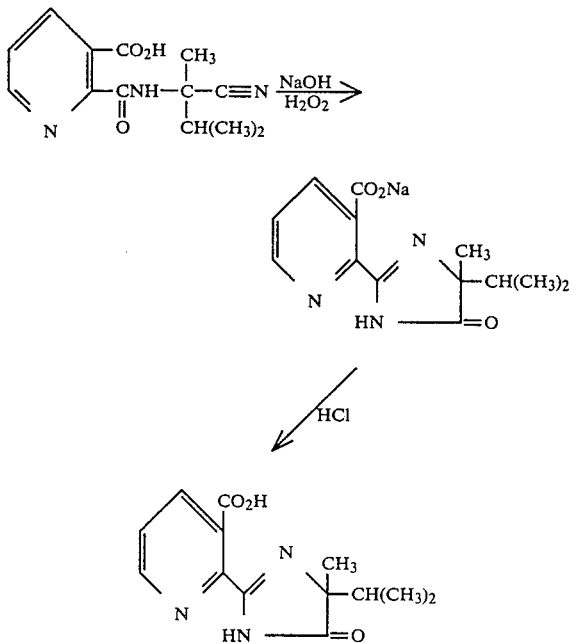

To a stirred mixture of 20 mL of water and 8.40 g (0.105 mol) of 50% sodium hydroxide solution is added 7.83 g (0.030 mol) of 2-[(1-cyano-1,2-dimethylpropyl)aminocarbonyl]-3-pyridinecarboxylic acid. External heating is applied to raise the temperature to 35°–40° C. To this solution 13.6 g (0.120 mol) of 30% hydrogen peroxide is added over 30 minutes while maintaining the temperature at 35°–40° C. with external cooling. After one and one-half hours at 35°–40° C., the mixture is heated to 70° C. and is held at that temperature for two hours. After cooling to 20°–30° C., 50 mL of methylene chloride is added and the pH is adjusted to 3.0 by the addition of 37% hydrochloric acid. The organic layer is separated and the solvent distilled off to give 7.57 g (87% yield) of solid 2-(5-isopropyl-5-methyl-4-oxo-2-imidazolin-2-yl)nicotinic acid.

EXAMPLE 12

Preparation of 2-(5-isopropyl-5-methyl-4-oxo-2-imidazolin-2-yl)-3-quinolinecarboxylic acid

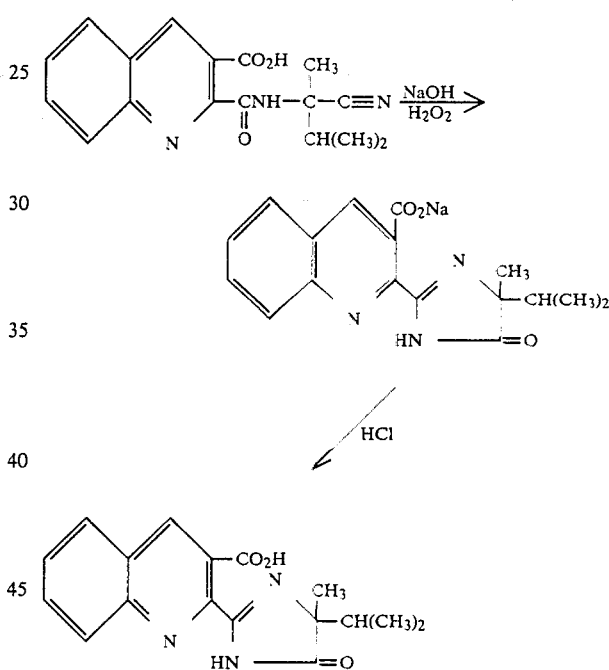

To a stirred solution of 1.69 g (0.042 mol) of solid sodium hydroxide in 11 mL of water is added 4.00 g (0.013 mol) of 2-[(1-cyano-1,2-dimethylpropyl)aminocarbonyl]-3-quinolinecarboxylic acid. External heating is applied to raise the temperature to 80°–83° C. To this solution 4.37 g (0.039 mol) of 30% hydrogen peroxide is added over 30 minutes while maintaining the temperature at 80°–83° C. After the hydrogen peroxide addition is complete, 1.04 g (0.026 mol) of solid sodium hydroxide is added. An additional 1.04 g (0.026 mol) of solid sodium hydroxide is added after 1 hour. Following a total reaction time of 2 hours, the solution is cooled in an ice-water bath and the pH is adjusted to 2.0 by the addition of 37% hydrochloric acid. The precipitate is filtered, washed, and dried to give 3.90 g (85% yield of solid 2-(5-isopropyl-5-methyl-4-oxo-2-imidazolin-2-yl)-3-quinolinecarboxylic acid which is 87.5% pure.

EXAMPLE 13

Effect of base stoichiometry and concentration on the formation of 2-(5,5-disubstituted-4-oxo-2-imidazolin-2-yl)compounds

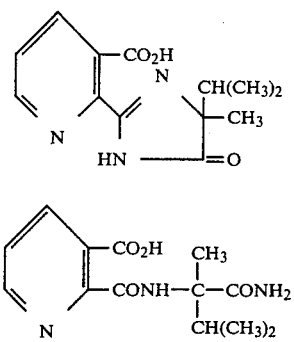

Three samples of 2-(5-isopropyl-5-methyl-4-oxo-2-imidazolin-2-yl)nicotinic acid (1.3 g, 0.005 mol) are dissolved in three 30% aqueous basic solutions containing, two, three and four molar equivalents of sodium hydroxide. Each of these solutions is heated at 60° C. for three hours and the solution anaylzed by high performance liquid chromatography for equilibrium concentrations of 2-(5-isopropyl-5-methyl-4-oxo-2-imidazolin-2-yl)nicotinic acid and 2-[(1-carbamoyl-1,2-dimethylpropyl)carbamoyl]nicotinic acid. Sufficient water is then added to each solution to adjust the base concentration to 15% and the equilibrium concentrations determined as above. Finally the base concentration is adjusted to 10% and the equilibrium concentrations determined. The results of these experiments illustrated graphically below demonstrate the importance of sufficient base concentration and stoichiometry for the efficient formation of the (2-imidazolin-2-yl) compounds.

EXAMPLE 14

Preparation of 2-(5-isopropyl-5-methyl-4-oxo-2-imidazolin-2-yl)-p-toluic acid and 6-(5-isopropyl-5-methyl-4-oxo-2-imidazolin-2-yl)-m-toluic acid

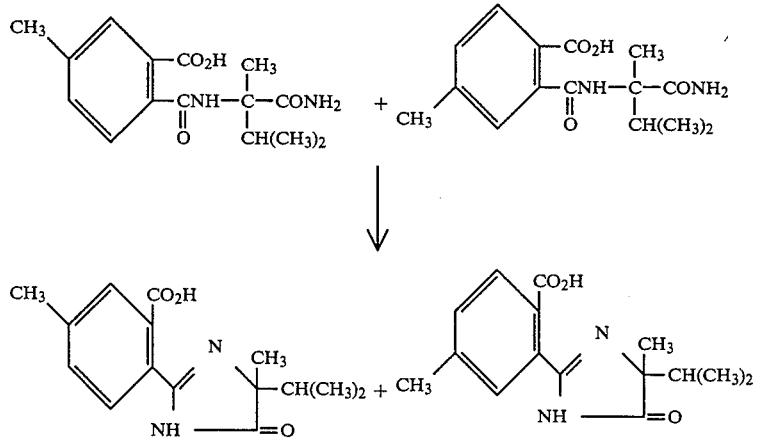

A mixture of the [(1-carbamoyl-1,2-dimethylpropyl)carbamoyl] meta and para toluic acids (5.83 g, 0.02 mol) is dissolved in 15% aqueous sodium hydroxide (0.4 mol, 20 molar equivalents). The solution is heated at 80° C. for two hours then cooled to room temperature. Analysis of the reaction mixture by high performance liquid chromatography shows 94% of the desired mixture of 2-(5-isopropyl-5-methyl-4-oxo-2-imidazolin-2-yl)-p-toluic acid and 6-(5-isopropyl-5-methyl-4-oxo-imidazolin-2-yl)-m-toluic acid.

EXAMPLE 15

Post-emergence herbicidal evaluation of test compounds

The post-emergence herbicidal activity of the compounds of the present invention is demonstrated by the following tests, wherein a variety of monocotyledonous and dicotyledonous plants are treated with test compounds and dispersed in aqueous acetone mixtures. In the tests, seedling plants are grown in jiffy flats for about 2 weeks. The test compounds are dispersed in 50/50 acetone/water mixtures containing 0.5% TWEEN ®20, a polyoxyethylene sorbitan monolaurate surfactant of Atlas Chemical Industries, in sufficient quantity to provide the equivalent of about 0.016 kg to 10 kg per hectare of active compound when applied to the plants through a spray nozzle operating at 40 psi for a predetermined time. After spraying, the plants are placed on greenhouse benches and are cared for in the usual manner commensurate with conventional greenhouse practices. From four to five weeks after treatment, the seedling plants are examined and rated according to the rating system provided below. The data obtained the recorded in Table I below.

| Rating System | % Difference in Growth from the Check* |
| --- | --- |
| 0 - No effect | 0 |
| 1 - Possible effect | 1–10 |
| 2 - Slight effect | 11–25 |
| 3 - Moderate effect | 26–40 |
| 5 - Definite injury | 41–60 |
| 6 - Herbicidal effect | 61–75 |
| 7 - Good herbicidal effect | 76–90 |
| 8 - Approaching complete kill | 91–99 |
| 9 - Complete kill | 100 |
| 4 - Abnormal growth, that is, a definite physiological malformation but with an overall effect less than a 5 on the rating scale. | |

In most cases, the data are for a single test, but in several instances, they are average values obtained from more than one test.

| Plant Species Used | |
|---|---|
| Barnyardgrass | (*Echinochloa crusgalli*) |
| Green foxtail | (*Setaria viridis*) |
| Purple Nutsedge | (*Cyperus rotundus* L.) |
| Wild Oats | (*Avena fatua*) |

| -continued | |
|---|---|
| Plant Species Used | |
| Quackgrass | *Agropyron repens*) |
| Field Bindweed | *Convolvulus arvensis* L.) |
| Morningglory | *Ipomoea purpurea*) |
| Ragweed | *Ambrosia artemisiifolia*) |
| Velvetleaf | *Abutilon theophrasti*) |
| Barley | *Hordeum vulgare*) |
| Corn | *Zea mays*) |
| Rice | *Oryza sativa*) |
| Soybean | *Glycine max*) |
| Sunflower | *Helianthus annus*) |
| Wheat | *Triticum aestivum*) |

TABLE I
POST-EMERGENCE TESTS -- RATES IN KG/HA

| Compound | RATE | BARNY ARDGR | GREEN FOX | P NUT SEDGE | WILD OATS | QUACK GRASS | FLD B INDWD | MRNGL RY SP | RAGWE ED | VELVE TLEAF | S BAR LY LA | CORN FIELD | RICE, NATO | SOYBE AN WI | SUNFL R XXX | S WHE AT ER |
|---|---|---|---|---|---|---|---|---|---|---|---|---|---|---|---|---|
| 2-(5-Isopropyl-5-methyl-4-oxo-2-imidazolin-2-yl)-nicotinic acid | 10.000 | 9.0 | 9.0 | 9.0 | 9.0 | | | 7.0 | 9.0 | 9.0 | | 9.0 | 9.0 | 9.0 | 9.0 | 9.0 |
| | 2.000 | 9.0 | 9.0 | 9.0 | 9.0 | | | 8.0 | 8.0 | 9.0 | 9.0 | 9.0 | 9.0 | 9.0 | 9.0 | 9.0 |
| | 1.000 | 9.0 | 9.0 | 9.0 | 9.0 | 9.0 | | 8.8 | 8.8 | 9.0 | 9.0 | 9.0 | 9.0 | 9.0 | 9.0 | 9.0 |
| | .500 | 9.0 | 9.0 | 8.7 | 9.0 | 9.0 | 8.8 | 8.8 | 8.6 | 8.9 | 9.0 | 9.0 | 8.8 | | 9.0 | 9.0 |
| | .250 | 8.9 | 9.0 | 8.8 | 9.0 | 9.0 | 9.0 | 8.9 | 8.6 | 8.9 | 9.0 | 9.0 | 8.8 | | 9.0 | 9.0 |
| 2-(4-oxo-1,3-diazospiro[4.5]dec-2-en-2-yl)-nicotinic acid | 1.000 | 9.0 | 9.0 | 7.0 | 9.0 | 7.0 | 9.0 | 4.0 | | 9.0 | 9.0 | 9.0 | 9.0 | | 9.0 | 9.0 |
| | .500 | 8.0 | 9.0 | 7.0 | 9.0 | 7.0 | 9.0 | 3.0 | 5.0 | 9.0 | 9.0 | 9.0 | 8.0 | 9.0 | 9.0 | 9.0 |
| | .250 | 6.0 | 9.0 | 7.0 | 9.0 | 7.0 | 9.0 | 1.0 | | 6.0 | 9.0 | 9.0 | 8.0 | 9.0 | 8.0 | 6.0 |
| 2-(5-Isopropyl-5-methyl-4-oxo-2-imidazolin-2-yl)-3-quinolinecarboxylic acid | 8.000 | 9.0 | 9.0 | 9.0 | 9.0 | 9.0 | 9.0 | 9.0 | 9.0 | 9.0 | 9.0 | 9.0 | 9.0 | 0.5 | 9.0 | 9.0 |
| | 4.000 | 9.0 | 9.0 | 8.5 | 9.0 | 9.0 | 9.0 | 8.5 | 8.5 | 9.0 | 9.0 | 9.0 | 9.0 | 0.0 | 9.0 | 9.0 |
| | 2.000 | 9.0 | 9.0 | 8.3 | 9.0 | 8.9 | 9.0 | 8.3 | 8.8 | 8.9 | | 9.0 | 9.0 | 0.1 | 9.0 | 8.9 |
| | 1.000 | 9.0 | 8.8 | 6.8 | | 8.8 | 8.7 | 8.3 | 8.0 | 8.6 | 9.0 | 9.0 | 8.7 | 3.0 | | |
| | .800 | 9.0 | 9.0 | 7.6 | 9.0 | 8.6 | 8.8 | 6.8 | 8.0 | 8.3 | | | | 4.0 | | 8.8 |
| | .500 | 8.9 | 8.8 | 9.0 | 9.0 | 9.0 | 9.0 | 7.7 | 8.4 | 7.7 | 9.0 | 9.0 | 8.3 | 2.7 | 9.0 | 9.0 |
| (+)-2-(5-Isopropyl-5-methyl-4-oxo-2-imidazolin-2-yl)-nicotinic acid | 1.000 | 9.0 | 9.0 | 9.0 | 9.0 | 9.0 | 9.0 | 9.0 | 9.0 | 9.0 | 9.0 | 9.0 | 9.0 | | 9.0 | 9.0 |
| | .500 | 9.0 | 9.0 | 9.0 | 9.0 | 9.0 | 9.0 | 9.0 | 9.0 | 9.0 | 9.0 | 9.0 | 9.0 | | 9.0 | 9.0 |
| 2-(5-Isopropyl-5-methyl-4-oxo-2-imidazolin-2-yl)-6-phenyl-nicotinic acid | 4.000 | 9.0 | 9.0 | 7.0 | 9.0 | 9.0 | 9.0 | 6.0 | 6.0 | 7.0 | | 9.0 | 8.0 | | 9.04 | 4.0 |
| | 1.000 | 9.0 | 9.0 | 3.0 | 7.0 | 2.0 | 6.0 | 4.0 | 4.0 | 2.0 | | 9.0 | 4.0 | | 9.0 | 2.0 |
| | .500 | 8.0 | 9.0 | 3.0 | 3.0 | | 8.0 | 3.0 | 1.0 | 2.0 | | 6.0 | | | 9.0 | 2.0 |
| | .250 | 8.0 | 7.0 | 2.0 | 2.0 | 2.0 | 5.0 | 1.0 | 0.0 | 0.0 | | 6.0 | 3.0 | | 9.0 | 1.0 |
| 2-(5-Isopropyl-5-methyl-4-oxo-2-imidazolin-2-yl)-6-methyl-nicotinic acid | 4.000 | 9.0 | 9.0 | 9.0 | 9.0 | 9.0 | 9.0 | 9.0 | 9.0 | 9.0 | | 9.0 | 9.0 | | 9.0 | 9.0 |
| | 1.000 | 9.0 | 9.0 | 9.0 | 9.0 | 9.0 | 9.0 | 9.0 | 8.5 | 9.0 | | 9.0 | 9.0 | | 9.0 | 9.0 |
| | .500 | 9.0 | 9.0 | 9.0 | 9.0 | 9.0 | 9.0 | 9.0 | 7.0 | 9.0 | | 9.0 | 9.0 | | 9.0 | 9.0 |
| | .250 | 9.0 | | 9.0 | 8.0 | 9.0 | 9.0 | 9.0 | | 6.0 | | 9.0 | 8.0 | | 8.0 | 9.0 |
| Methyl 5-ethyl-2-(5-isopropyl-5-methyl-4-oxo-2-imidazolin-2-yl)nicotinate | 1.000 | 9.0 | | 9.0 | 9.0 | 9.0 | 9.0 | 9.0 | 9.0 | 9.0 | | 9.0 | 9.0 | | 9.0 | 9.0 |
| | .500 | 9.0 | | 9.0 | 9.0 | 9.0 | 9.0 | 9.0 | 9.0 | 9.0 | | 9.0 | 9.0 | | 9.0 | 9.0 |
| | .250 | 9.0 | | 9.0 | 9.0 | 9.0 | 9.0 | 9.0 | 9.0 | 8.0 | | 9.0 | 9.0 | | 9.0 | 9.0 |
| 6-Ethyl-2-(5-isopropyl-5-methyl-4-oxo-2-imidazolin-2-yl)nicotinic acid | 1.000 | 9.0 | | 9.0 | 9.0 | 9.0 | 9.0 | 9.0 | 9.0 | 9.0 | | 9.0 | 9.0 | | 9.0 | 9.0 |
| | .500 | 8.0 | | 9.0 | 9.0 | 9.0 | 9.0 | 9.0 | 9.0 | 9.0 | | 9.0 | 9.0 | | 9.0 | 8.0 |
| | .250 | 8.0 | | 9.0 | 8.0 | 9.0 | 9.0 | 9.0 | 9.0 | 8.0 | | 9.0 | 8.0 | | 9.0 | 6.0 |
| 2-(5-Isopropyl-5-methyl-4-oxo-2-imidazolin-2-yl)-quinolinecarboxylic acid | 1.000 | 9.0 | | 7.0 | 9.0 | 6.0 | 8.0 | 8.0 | 9.0 | 5.0 | | 8.0 | 5.0 | | 8.0 | 5.0 |
| | .500 | 9.0 | | 6.0 | 9.0 | 4.0 | 9.0 | 8.0 | 9.0 | 2.0 | | 8.0 | 4.0 | | 7.0 | 7.0 |
| | .250 | 9.0 | | 1.0 | 4.0 | 3.0 | 7.0 | 7.0 | 8.0 | 1.0 | | 6.0 | 1.0 | | 6.0 | 3.0 |
| 2-(5-Isopropyl-5-methyl-4-oxo-2-imidazolin-2-yl)-6-propyl-nicotinic acid | 1.000 | 9.0 | | 8.0 | 9.0 | 9.0 | 8.0 | 9.0 | 9.0 | 9.0 | | 9.0 | 9.0 | | 9.0 | 9.0 |
| | .500 | 8.0 | | 7.0 | 8.0 | 9.0 | 9.0 | 9.0 | 8.0 | 9.0 | | 9.0 | 9.0 | | 9.0 | 9.0 |

4,518,780

TABLE I-continued

POST-EMERGENCE TESTS -- RATES IN KG/HA

| Compound | RATE | BARNY ARDGR | GREEN FOX | P NUT SEDGE | WILD OATS | QUACK GRASS | FLD B INDWD | MRNGL RY SP | RAGWE ED | VELVE TLEAF | S BAR LY LA | CORN FIELD | RICE, NATO | SOYBE AN WI | SUNFL R XXX | S WHE AT ER |
|---|---|---|---|---|---|---|---|---|---|---|---|---|---|---|---|---|
| 2-(5-Isopropyl-5-methyl-4-oxo-2-imidazolin-2-yl)-6-methoxy-3-quinoline-carboxylic acid | 8.000 1.000 .500 .250 | 9.0 9.0 9.0 6.0 | 9.0 | 9.0 2.0 1.0 1.0 | 9.0 9.0 9.0 9.0 | 9.0 8.0 7.0 5.0 | 9.0 9.0 6.0 | 9.0 6.0 2.0 0.0 | 9.0 7.0 7.0 3.0 | 9.0 3.0 3.0 | | 9.0 9.0 9.0 | 9.0 7.0 9.0 | | 9.0 9.0 9.0 | 6.0 4.0 4.0 |
| 5,6,7,8-Tetrahydro-2-(5-Isopropyl-5-methyl-4-oxo-2-imidazolin-2-yl)-3-quinolinecarboxylic acid | 1.000 .500 .250 | 9.0 9.0 6.0 | | 8.0 6.0 7.0 | 9.0 9.0 9.0 | 9.0 9.0 9.0 | 9.0 9.0 9.0 | 9.0 9.0 7.0 | 3.0 2.0 0.0 | 9.0 9.0 3.0 | | 9.0 9.0 9.0 | 9.0 9.0 9.0 | | 9.0 9.0 9.0 | 9.0 9.0 9.0 |
| 2-(5-Isopropyl-5-methyl-4-oxo-2-imidazolin-2-yl)-5,6-dimethyl-nicotinic acid | 5.000 1.000 .500 .250 | 9.0 4.0 4.0 4.0 | 9.0 | 9.0 9.0 9.0 9.0 | | 9.0 9.0 9.0 9.0 | 9.0 9.0 9.0 9.0 | 9.0 9.0 9.0 9.0 | 9.0 9.0 8.0 8.0 | 9.0 9.0 9.0 9.0 | 9.0 | 9.0 9.0 9.0 | 9.0 9.0 9.0 | 9.0 | 9.0 9.0 9.0 | 9.0 9.0 |
| (+)-2-(5-Isopropyl-5-methyl-4-oxo-2-imidazolin-2-yl)-3-quinolinecarboxylic acid | 1.000 .800 .500 .400 .300 | 9.0 9.0 9.0 8.8 8.8 | 9.0 9.0 9.0 9.0 8.8 | 7.0 7.3 6.8 6.8 6.8 | | 8.8 9.0 8.8 8.3 7.8 | 8.8 9.0 9.0 9.0 8.7 | 8.0 7.8 7.0 7.0 6.3 | 9.0 9.0 8.8 7.8 8.0 | 8.8 9.0 8.8 8.0 7.3 | | | | 5.5 5.0 4.8 3.8 4.3 | | |
| 6,7-Dihydro-2-(5-isopropyl-5-methyl-4-oxo-2-imidazolin-2-yl)-5H—pyrindine-3-carboxylic acid | 1.000 .500 .250 | 9.0 8.0 8.0 | | 9.0 8.0 8.0 | 9.0 9.0 9.0 | 9.0 9.0 9.0 | 9.0 9.0 9.0 | 9.0 9.0 9.0 | 9.0 9.0 8.0 | 9.0 9.0 9.0 | | 9.0 9.0 9.0 | 9.0 9.0 9.0 | | 9.0 9.0 9.0 | 9.0 9.0 9.0 |
| 2-(5-Isopropyl-5-methyl-4-oxo-2-imidazolin-2-yl)-6-(trifluoromethyl)-nicotinic acid | 1.000 .500 .250 | 7.0 6.0 6.0 | | 9.0 7.0 7.0 | 9.0 9.0 9.0 | 9.0 9.0 9.0 | 9.0 9.0 9.0 | 9.0 8.0 9.0 | 9.0 9.0 8.0 | 9.0 9.0 9.0 | | 9.0 9.0 9.0 | 9.0 7.0 7.0 | | 9.0 9.0 9.0 | 9.0 9.0 9.0 |
| 2-(5-Isopropyl-5-methyl-4-oxo-2-imidazolin-2-yl)-3-quinolinecarboxylic acid | 1.000 .500 .250 | 8.0 6.0 2.0 | | 0.0 0.0 0.0 | 9.0 8.0 7.0 | 0.0 4.0 1.0 | 2.0 1.0 0.0 | 2.0 1.0 1.0 | 9.0 8.0 | 3.0 1.0 0.0 | | 8.0 7.0 7.0 | 5.0 5.0 2.0 | | 9.0 9.0 9.0 | 9.0 6.0 5.0 |
| 6-(Difluoromethoxy)-2-(5-isopropyl-5-methyl-4-oxo-2-imidazolin-2-yl)-3-quinolinecarboxylic acid | 1.000 .500 .250 | 9.0 8.0 8.0 | | 0.0 0.0 0.0 | 9.0 9.0 9.0 | 7.0 4.0 4.0 | 9.0 4.0 1.0 | 9.0 8.0 7.0 | 9.0 | 4.0 3.0 1.0 | | 9.0 9.0 9.0 | 7.0 6.0 5.0 | | 9.0 9.0 9.0 | 9.0 9.0 9.0 |

EXAMPLE 16

Preemergence Herbicidal Evaluation of Test Compounds

The preemergence herbicidal activity of the compounds of the present invention is exemplified by the following tests in which the seeds of a variety of monocotyledonous and dicotyledonous plants are separately mixed with potting soil and planted on top of approximately one inch of soil in separate pint cups. After planting, the cups are sprayed with the selected aqueous acetone solution containing test compound in sufficient quantity to provide the equivalent of about 0.016 to 10 kg per hectare of test compound per cup. The treated cups are then placed on greenhouse benches, watered, and cared for in accordance with conventional greenhouse procedures. From four to five weeks after treatment, the tests are terminated, and each cup is examined and rated according to the rating system set forth above. The herbicidal proficiency of the active ingredients of the present invention is evident from the test results which are recorded in Table II below. Where more than one test is involved for a given compound, the data are averaged.

TABLE II

PRE-EMERGENCE TESTS -- RATES IN KG/HA

| Compound | RATE | BARN-YARDGR | GREEN FOX | P NUT SEDGE | WILD OATS | QUACK GRASS | FLD B INDWD | MRNGLRY SP | RAG-WEED | VELVET LEAF | S BARLY LA | CORN FIELD | RICE, NATO | SOY-BEAN WI | SUNFLR XXX | S WHEAT ER |
|---|---|---|---|---|---|---|---|---|---|---|---|---|---|---|---|---|
| 2-(5-Isopropyl-5-methyl-4-oxo-2-imidazolin-2-yl)-nicotinic acid | 10.000 | 8.0 | 9.0 | 9.0 | 8.0 | | | 8.0 | 8.0 | 8.0 | | 9.0 | 9.0 | 8.0 | | 9.0 |
| | 2.000 | 9.0 | 9.0 | 9.0 | 9.0 | | | 8.0 | 9.0 | 9.0 | 9.0 | 9.0 | 9.0 | 8.5 | 9.0 | 9.0 |
| | 1.000 | 9.0 | 9.0 | 9.0 | 9.0 | 9.0 | 9.0 | 8.7 | 8.8 | 8.8 | 9.0 | 9.0 | 9.0 | 8.7 | 9.0 | 9.0 |
| | .500 | 9.0 | 9.0 | 9.0 | 9.0 | 9.0 | 9.0 | 8.8 | 8.8 | 8.8 | 9.0 | 9.0 | 9.0 | 8.7 | 9.0 | 9.0 |
| | .250 | 9.0 | 9.0 | 9.0 | 9.0 | | | | | | 9.0 | 9.0 | 9.0 | | 9.0 | 7.0 |
| 2-(4-oxo-1,3-diazospiro[4.5]dec-2-en-2-yl)-nicotinic acid | 2.000 | | | | | | | | | | 8.5 | 4.5 | | | | 4.0 |
| | 1.000 | 6.0 | 8.0 | 8.0 | 6.0 | 7.0 | 9.0 | 8.0 | 7.0 | 9.0 | 5.0 | 1.5 | 9.0 | | 1.0 | 9.0 |
| | .500 | 1.0 | 7.0 | 2.0 | 3.0 | 1.0 | 9.0 | 3.0 | 3.0 | 9.0 | | | 8.0 | | 0.0 | 9.0 |
| 2-(5-Isopropyl-5-methyl-4-oxo-2-imidazolin-2-yl)-3-quinoline-carboxylic acid | 8.000 | 9.0 | 9.0 | 9.0 | 9.0 | 9.0 | | 9.0 | 9.0 | 9.0 | | 9.0 | 9.0 | | 9.0 | 9.0 |
| | 4.000 | 9.0 | 9.0 | 9.0 | 9.0 | 9.0 | | 9.0 | 9.0 | 9.0 | 9.0 | 9.0 | 9.0 | | 9.0 | 9.0 |
| | 1.000 | 9.0 | 9.0 | 9.0 | 9.0 | 9.0 | | 9.0 | 9.0 | 8.8 | 9.0 | 9.0 | 9.0 | 6.5 | 8.7 | 8.9 |
| | .500 | 8.3 | 9.0 | 9.0 | 8.9 | 9.0 | | 8.6 | 8.8 | 8.5 | 9.0 | 8.8 | 9.0 | 4.0 | 8.6 | 8.6 |
| | .250 | 9.0 | 8.8 | 9.0 | 8.6 | 9.0 | | 8.0 | 7.9 | 7.9 | 9.0 | 9.0 | 9.0 | 3.6 | 9.0 | 9.0 |
| (±)-2-(5-Isopropyl-5-methyl-4-oxo-2-imidazolin-2-yl)-nicotinic acid | .500 | 9.0 | | 9.0 | 9.0 | 9.0 | | 9.0 | 9.0 | 9.0 | 9.0 | 9.0 | 9.0 | | 9.0 | 9.0 |
| | .250 | 9.0 | | 9.0 | 9.0 | 9.0 | | 9.0 | 9.0 | 9.0 | 9.0 | 9.0 | 9.0 | | 9.0 | 9.0 |
| 2-(5-Isopropyl-5-methyl-4-oxo-2-imidazolin-2-yl)-6-phenyl-nicotinic acid | 4.000 | 3.0 | 4.0 | 9.0 | 3.0 | 9.0 | 9.0 | 4.0 | 4.0 | 7.0 | | 9.0 | 7.0 | | 9.0 | 5.0 |
| | 1.000 | 2.0 | 4.0 | 9.0 | 9.0 | 9.0 | 9.0 | 4.0 | 6.0 | 6.0 | | 9.0 | 5.0 | | 9.0 | 5.0 |
| | .500 | 2.0 | 4.0 | 9.0 | 9.0 | 9.0 | 9.0 | | | 5.0 | | | | | 9.0 | 5.0 |
| 2-(5-Isopropyl-5-methyl-4-oxo-2-imidazolin-2-yl)-6-methyl-nicotinic acid | 4.000 | 9.0 | 9.0 | 9.0 | 9.0 | 9.0 | 9.0 | 9.0 | 9.0 | 9.0 | | 9.0 | 9.0 | | 9.0 | 9.0 |
| | 1.000 | 9.0 | 9.0 | 9.0 | 9.0 | 9.0 | 9.0 | 9.0 | 9.0 | 9.0 | | 9.0 | 9.0 | | 9.0 | 9.0 |
| | .500 | 9.0 | 9.0 | 9.0 | 9.0 | 9.0 | 9.0 | 9.0 | 9.0 | 9.0 | | 9.0 | 9.0 | | 9.0 | 9.0 |
| | .250 | 9.0 | 9.0 | 9.0 | 9.0 | 9.0 | 9.0 | 9.0 | 9.0 | 9.0 | | 9.0 | 9.0 | | 9.0 | 9.0 |
| Methyl 5-ethyl-2-(5-isopropyl-5-methyl-4-oxo-2-imidazolin-2-yl)nicotinate | .500 | 9.0 | 9.0 | 9.0 | 9.0 | 9.0 | 9.0 | 9.0 | 9.0 | 9.0 | | 9.0 | 9.0 | 9.0 | 9.0 | 9.0 |
| | .250 | 9.0 | 9.0 | 9.0 | 9.0 | 9.0 | 9.0 | 9.0 | 7.0 | 9.0 | | 9.0 | 9.0 | 9.0 | 9.0 | 9.0 |
| 6-Ethyl-2-(5-isopropyl-5-methyl-4-oxo-2-imidazolin-2-yl)-nicotinic acid | .500 | 9.0 | 9.0 | 9.0 | 9.0 | 9.0 | 9.0 | 9.0 | 9.0 | 9.0 | | 9.0 | 9.0 | | 9.0 | 9.0 |
| | .250 | 9.0 | 8.0 | 9.0 | 7.0 | 8.0 | 9.0 | 7.0 | 9.0 | 8.0 | | 9.0 | 9.0 | | 9.0 | 7.0 |
| 2-(5-Isopropyl-5-methyl-4-oxo-2-imidazolin-2-yl)-6-nitro-3-quinollnecarbo-xylic acid | 4.000 | 9.0 | 9.0 | 8.0 | 9.0 | 9.0 | 9.0 | 9.0 | 8.0 | 9.0 | | 9.0 | 9.0 | | 9.0 | 9.0 |
| | 1.000 | 9.0 | 9.0 | 9.0 | 9.0 | 9.0 | 9.0 | 9.0 | 8.0 | 7.0 | | 9.0 | 9.0 | | 8.0 | 9.0 |
| | .500 | 8.5 | 8.0 | 7.0 | 7.0 | 9.0 | 9.0 | 8.5 | 7.5 | 6.0 | | 8.5 | 9.0 | | 8.0 | 8.5 |
| | .250 | 9.0 | | 3.0 | 8.0 | 9.0 | 9.0 | 8.0 | 9.0 | 4.0 | | 9.0 | 9.0 | | 8.0 | 7.0 |
| 2-(5-Isopropyl-5-methyl-4-oxo-2-imidazolin-2-yl)-6-propyl | .500 | 8.0 | | 9.0 | 7.0 | 7.0 | 9.0 | 7.0 | 6.0 | 8.0 | | 9.0 | 9.0 | | 7.0 | 7.0 |
| | .250 | 4.0 | | 8.0 | 5.0 | 8.0 | 9.0 | 7.0 | 6.0 | 7.0 | | 6.0 | 9.0 | | 6.0 | 4.0 |

TABLE II-continued
PRE-EMERGENCE TESTS -- RATES IN KG/HA

| Compound | RATE | BARN-YARDGR | GREEN FOX | P NUT SEDGE | WILD OATS | QUACK GRASS | FLD B INDWD | MRNGLRY SP | RAG-WEED | VELVET LEAF | S BARLY LA | CORN FIELD | RICE, NATO | SOY-BEAN WI | SUNFLR XXX | S WHEAT ER |
|---|---|---|---|---|---|---|---|---|---|---|---|---|---|---|---|---|
| nicotinic acid 2-(5-Isopropyl-5-methyl-4-oxo-2-imidazolin-2-yl)-6-methoxy-3-quinoline-carboxylic acid | 8.000 | 9.0 | 9.0 | 9.0 | 9.0 | 9.0 | 9.0 | 8.0 | 9.0 | 8.0 | | | | | | |
|  | .500 | 9.0 |  | 9.0 | 8.0 | 9.0 | 9.0 | 8.0 | 9.0 | 8.0 | | 9.0 | 9.0 | | 9.0 | 6.0 |
|  | .250 | 7.0 |  | 7.0 | 7.0 | 9.0 | 9.0 | 6.0 | 7.0 | 7.0 | | 7.0 | 9.0 | | 9.0 | 6.0 |
| 5,6,7,8-Tetrahydro-2-(5-Isopropyl-5-methyl-4-oxo-2-imidazolin-2-yl)-3-quinolinecarboxylic acid | .500 | 9.0 |  | 9.0 | 9.0 | 9.0 | 9.0 | 9.0 | 9.0 | 9.0 | | 9.0 | 9.0 | | 9.0 | 9.0 |
|  | .250 | 6.0 |  | 8.0 | 7.0 | 9.0 | 9.0 | 8.0 | 7.0 | 8.0 | | 8.0 | 9.0 | | 6.5 | 8.0 |
| 2-(5-Isopropyl-5-methyl-4-oxo-2-imidazolin-2-yl)-5,6-dimethyl-nicotinic acid | 5.000 | 9.0 | 9.0 | 9.0 | 8.0 | 9.0 | 9.0 | 5.0 | 9.0 | 8.0 | | | | | | |
|  | .500 | 8.0 |  | 9.0 | 9.0 | 9.0 | 9.0 | 9.0 | 9.0 | 9.0 | | 9.0 | 9.0 | | 9.0 | 9.0 |
|  | .250 | 9.0 |  | 9.0 | 8.0 | 9.0 | 9.0 | 9.0 | 6.0 | 9.0 | | 9.0 | 9.0 | | 8.0 | 9.0 |
| 6,7-Dihydro-2-(5-isopropyl-5-methyl-4-oxo-2-imidazolin-2-yl)-5H—1-pyrindine-3-carboxylic acid | .500 | 9.0 |  | 9.0 | 8.0 | 9.0 | 9.0 | 9.0 | 9.0 | 8.0 | | 9.0 | 9.0 | | 9.0 | 9.0 |
|  | .250 | 9.0 |  | 9.0 | 9.0 | 9.0 | 9.0 | 8.0 | 8.0 | 9.0 | | 9.0 | 9.0 | | 9.0 | 9.0 |
| 2-(5-Isopropyl-5-methyl-4-oxo-2-imidazolin-2-yl)-6-(trifluoromethyl)-nicotinic acid | .500 | 1.0 |  | 9.0 | 9.0 | 9.0 | 9.0 | 8.0 | 9.0 | 7.0 | | 9.0 | 9.0 | | 9.0 | 9.0 |
|  | .250 | 1.0 |  | 9.0 | 9.0 | 9.0 | 9.0 | 9.0 | 1.0 | 7.0 | | 9.0 | 9.0 | | 9.0 | 9.0 |
| 2-(5-Isopropyl-5-methyl-4-oxo-2-imidazolin-2-yl)-6-p-tolylnicotinic acid | .500 | 8.0 | 0.0 | 6.0 | 4.0 | 9.0 | 4.0 | 8.0 | 0.0 | 6.0 | 8.0 | 7.0 | 5.0 | 6.0 | 7.0 | 2.0 |
|  | .250 | 2.0 | 0.0 | 3.0 | 1.0 | 4.0 | 3.0 | 3.0 | 0.0 | 3.0 | 2.0 | 2.0 | 3.0 | 5.0 | 6.0 | 1.0 |
| 2-(5-Isopropyl-5-methyl-4-oxo-2-imidazolin-2-yl)-6-(trifluoromethyl)-3-quinolinecarboxylic acid | .500 | 7.0 | 2.0 | 9.0 | 9.0 | 9.0 | 8.0 | 9.0 | 5.0 | | | 9.0 | | 9.0 | 8.0 | |
|  | .250 | 5.0 | 1.0 | 8.0 | 4.0 | 9.0 | 1.0 | 8.0 | 2.0 | | | 7.0 | | 9.0 | 7.0 | |
| 6-(Difluoromethoxy)-2-(5-isopropyl-5-methyl-4-oxo-2-imidazolin-2-yl)-3-quinolinecarboxylic acid | .500 | 9.0 | 2.0 | 9.0 | 9.0 | 9.0 | 9.0 | 9.0 | 8.0 | | 9.0 | 9.0 | | 9.0 | 9.0 | |
|  | .250 | 5.0 | 1.0 | 9.0 | 9.0 | 9.0 | 9.0 | 9.0 | 7.0 | | 9.0 | 9.0 | | 9.0 | 8.0 | |

EXAMPLE 17

Effect of base concentration on the formation of 2-(5,5-disubstituted-4-oxo-2-imidazolin-2-yl) compounds Samples of 2[(1-carbamoyl-1,2-dimethylpropyl)carbamoyl]nicotinic acid, meta and para-toluic acids are dissolved in 3.42 molar equivalents of aqueous sodium hydroxide at varying concentrations of 4%, 10%, and 20%. The resulting solutions are heated at 80° to 85° C. for two to three hours and the solutions assayed for the desired cyclized (imidazolin-2-yl) products. The results of these experiments are reported in Table III below, which demonstrates a significant increase in product formation at base concentrations of 10% or greater on weight basis.

TABLE III

Effect of base concentration of the formation of (imidazolin-2-yl) compounds of the invention

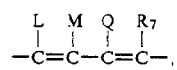

| R | NaOH Concentration | Time hrs | % yield |
|---|---|---|---|
| (p-methylphenyl) | 4 | 0.083 | 17.7 |
|  | 4 | 3.0 | 81.8 |
|  | 10 | 3.0 | 94.0 |
| + |  |  |  |
| (m-methylphenyl) |  |  |  |
| (pyridyl) | 4 | 3.0 | 87.4 |
|  | 10 | 3.0 | 96.5 |
|  | 20 | 3.0 | 98.1 |

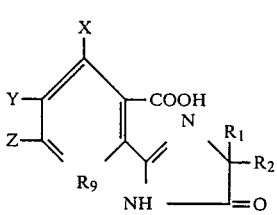

What is claimed is:

1. A process for the preparation of a 2-(5,5-disubstituted-4-oxo-2-imidazolin-2-yl)nicotinic acid, 3-quinolinecarboxylic acid or benzoic acid of the formula:

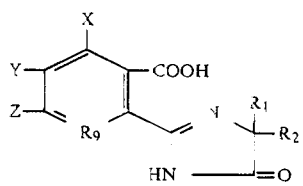

wherein $R_9$ is N or CH; $R_1$ is $C_1$-$C_4$ alkyl; $R_2$ is $C_1$-$C_4$ alkyl or $C_3$-$C_6$ cycloalkyl; and when $R_1$ and $R_2$ are taken together along with the carbon to which they are attached, they may represent $C_3$-$C_6$ cycloalkyl optionally substituted with methyl, and when $R_1$ and $R_2$ are not the same, the optical isomers thereof; X is hydrogen, or $C_1$-$C_4$ alkyl, Y is hydrogen, halogen, $C_1$-$C_4$ alkyl, $C_1$-$C_4$ alkoxy, trifluoromethyl, trichloromethyl, difluoromethoxy, diloweralkylamino, $C_1$-$C_4$ alkylthio, nitro, phenyl or phenoxy optionally substituted with one $C_1$-$C_4$ alkyl, $C_1$-$C_4$ alkoxy or halogen; Z is hydrogen, $C_1$-$C_4$ alkyl, trifluoromethyl, trichloromethyl, phenyl or phenyl substituted with one $C_1$-$C_4$ alkyl, $C_1$-$C_4$ alkoxy or halogen; and when taken together, Y and Z may form a ring in which YZ are represented by the structure: $-(CH_2)_n-$, where n is an integer from 3 to 5, provided that X is hydrogen; or YZ is $$\begin{array}{cccc} L & M & Q & R_7 \\ | & | & | & | \\ -C= & C- & C= & C- \end{array},$$

where L, M, Q and $R_7$ are each hydrogen, halogen, $C_1$-$C_4$ alkyl, $C_1$-$C_4$ alkoxy, $C_1$-$C_4$ haloalkyl, difluoromethoxy, diloweralkylamino, $C_1$-$C_4$ alkylthio, nitro, phenyl, phenoxy or mono-substituted phenyl or phenoxy where the substituent is $C_1$-$C_4$ alkoxy or halogen; with the proviso that only one of L, M, Q or $R_7$, may represent a substituent other than hydrogen, halogen, $C_1$-$C_4$ alkyl or $C_1$-$C_4$ alkoxy; comprising, reacting a compound of the structure:

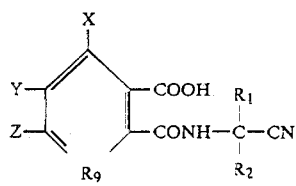

wherein $R_9$, X, Y, Z, W, $R_1$ and $R_2$ are as described above, with from 2 to 20 molar equivalents of an aqueous or aqueous alcoholic sodium or potassium hydroxide of a concentration of 10% or greater and from 0 to 10 molar equivalents of 30 to 90% aqueous hydrogen peroxide at a temperature of from 25° to 100° C. and thereafter acidifying the thus-formed reaction mixture to a pH between 2 and 4 with a strong mineral acid to give the formula (I) acid.

2. A process according to claim 1, wherein the base concentration is from 10 to 40% of the total reaction mixture on a weight basis, used in sufficient quantities to provide from two to six molar equivalents of base for each equivalent of acid amidonitrile reactant.

3. A process for the preparation of a compound having the structure: (IA):

wherein $R_9$ is N or CH; $R_1$ is $C_1$-$C_4$ alkyl; $R_2$ is $C_1$-$C_4$ alkyl or $C_3$-$C_6$ cycloalkyl; and when $R_1$ and $R_2$ are taken together along with the carbon to which they attached, they may represent $C_3$–$C_6$ cycloalkyl optionally substituted with methyl, and when $R_1$ and $R_2$ are not the same, the optical isomers thereof; X is hydrogen, or $C_1$–$C_4$ alkyl, Y is hydrogen, halogen, $C_1$–$C_4$ alkyl, $C_1$–$C_4$ alkoxy, trifluoromethyl, trichloromethyl, difluoromethoxy, diloweralkylamino, $C_1$–$C_4$ alkylthio, nitro, phenyl or phenoxy optionally substituted with one $C_1$–$C_4$ alkyl, $C_1$–$C_4$ alkoxy or halogen; Z is hydrogen, $C_1$–$C_4$ alkyl, trifluoromethyl, trichloromethyl, phenyl or phenyl substituted with one $C_1$–$C_4$ alkyl, $C_1$–$C_4$ alkoxy or halogen; and when taken together, Y and Z may form a ring in which YZ are represented by the structure: —$(CH_2)_n$—, where n is an integer from 3 to 5, provided that X is hydrogen; or YZ is

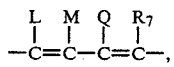

where L, M, Q and $R_7$ are each hydrogen, halogen $C_1$–$C_4$ alkyl, $C_1$–$C_4$ alkoxy, $C_1$–$C_4$ haloalkyl, difluoromethoxy, diloweralkylamino, $C_1$–$C_4$ alkylthio, nitro, phenyl, phenoxy or monosubstituted phenyl or phenoxy where the substituent is $C_1$–$C_4$ alkoxy or halogen; with the proviso that only one of L, M, Q or $R_7$, may represent a substituent other than hydrogen, halogen, $C_1$–$C_4$ alkyl or $C_1$–$C_4$ alkoxy; comprising, reacting a compound of the formula:

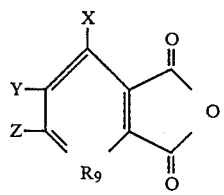

with an equivalent amount of a compound of the formula:

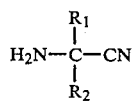

in the presence of a solvent of diethyl ether, tetrahydrofuran, dimethoxyethane, acetonitrile or a low-boiling halogenated hydrocarbon, at a temperature between 20° and 60° C. under a blanket of nitrogen, to obtain an isomeric mixture of the compounds having the structures (a) and (b):

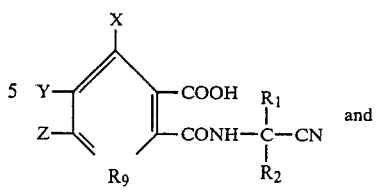

(a)

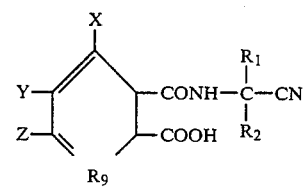

(b)

treating the thus-formed reaction product with 2 to 10 moles of aqueous or aqueous $C_1$–$C_4$ alcoholic sodium or potassium hydroxide and 2 to 5 moles of 30 to 90% aqueous hydrogen peroxide per mole of formula (a) and (b) compound, at a temperature of 25° to 110° C., acidifying the thus-formed reaction mixture to a pH between 2 and 4 with hydrochloric acid or sulfuric acid, extracting the acidified reaction mixture with an organic solvent and separating the solvent from the formula (IA) acid product.

4. A process according to claim 1 wherein $R_1$ is methyl; $R_2$ is isopropyl; X is hydrogen; Y is hydrogen, halogen, $C_1$–$C_4$ alkyl, $C_1$–$C_4$ alkoxy, trifluoromethyl, trichloromethyl, difluoromethoxy, diloweralkylamino, $C_1$–$C_4$ alkylthio, nitro, phenyl, phenoxy, or phenyl or phenoxy substituted with one $C_1$–$C_4$ alkyl, $C_1$–$C_4$ alkoxy or halogen and Z represents hydrogen, $C_1$–$C_4$ alkyl, trifluoromethyl, trichloromethyl, phenyl or phenyl substituted with one $C_1$–$C_4$ alkyl, $C_1$–$C_4$ alkoxy or halogen.

5. A process according to claim 1 wherein $R_1$ is methyl; $R_2$ is isopropyl; X is hydrogen and Y and Z are taken together to form a ring in which YZ represents

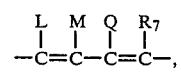

where L, M, Q and $R_7$ each are hydrogen, halogen, $C_1$–$C_4$ alkyl, $C_1$–$C_4$ alkoxy, $C_1$–$C_4$ haloalkyl, difluoromethoxy, diloweralkylamino, $C_1$–$C_4$ alkylthio, nitro, phenyl, phenoxy or substituted phenyl or phenoxy where the substituent is one $C_1$–$C_4$ alkyl, $C_1$–$C_4$ alkoxy or halogen; with the proviso that only one of L, M, Q or $R_7$ may represent a substituent other than hydrogen, halogen, $C_1$–$C_4$ alkyl or $C_1$–$C_4$ alkoxy.

6. A process according to claim 1 for the preparation of (+)-2-(5-isopropyl-5-methyl-4-oxo-2-imidazolin-2-yl)-3-quinolinecarboxylic acid.

7. A process according to claim 1 for the preparation of (+)-2-(5-isopropyl-5-methyl-4-oxo-2-imidazolin-2-yl)nicotinic acid.

8. A process according to claim 1 for the preparation of the mixture of compounds 2-(5-isopropyl-5-methyl-4-oxo-2-imidazolinyl-2-yl)-p-toluic acid and 6-(5-isopropyl-5-methyl-4-oxo-2-imidazolin-2-yl)-m-toluic acid.

* * * * *